(12) United States Patent
Jarho et al.

(10) Patent No.: US 7,592,328 B2
(45) Date of Patent: Sep. 22, 2009

US007592328B2

(54) NATURAL CYCLODEXTRIN COMPLEXES

(75) Inventors: Pekka Jarho, Kuopio (FI); Janne Mannila, Kuopio (FI); Tomi Järvinen, Kuopio (FI)

(73) Assignee: Pedipharm Oy, Kuopio (FI)

( * ) Notice: Subject to any disclaimer, the term of this patent is extended or adjusted under 35 U.S.C. 154(b) by 272 days.

(21) Appl. No.: 10/505,136

(22) PCT Filed: Feb. 20, 2003

(86) PCT No.: PCT/FI03/00126

§ 371 (c)(1), (2), (4) Date: Sep. 16, 2004

(87) PCT Pub. No.: WO03/070775

PCT Pub. Date: Aug. 28, 2003

(65) Prior Publication Data

US 2005/0153931 A1    Jul. 14, 2005

(30) Foreign Application Priority Data

Feb. 20, 2002    (FI) .................................. 20020334

(51) Int. Cl.
*A61K 31/05* (2006.01)
*A61K 31/366* (2006.01)
*A61K 31/724* (2006.01)

(52) U.S. Cl. .................... 514/58; 514/455; 514/738

(58) Field of Classification Search .................... 514/58, 514/455, 738
See application file for complete search history.

(56) References Cited

U.S. PATENT DOCUMENTS

| | | | |
|---|---|---|---|
| 4,596,795 A | 6/1986 | Pitha | |
| 4,599,327 A | 7/1986 | Nogradi et al. | |
| 5,070,081 A * | 12/1991 | Majid et al. | .................... 514/58 |
| 5,180,716 A | 1/1993 | Yaksh et al. | |
| 6,383,513 B1 | 5/2002 | Watts et al. | |
| 7,115,586 B2 | 10/2006 | Loftsson | |
| 2005/0090468 A1 | 4/2005 | Jarvinen et al. | |

FOREIGN PATENT DOCUMENTS

WO    WO 99/32107 A1    7/1999

OTHER PUBLICATIONS

Williamson, E. et al "Cannabinoids in clinical practice" Drugs (2000) vol. 60, No. 6, pp. 1303-1314.*
Loftsson, T. et al "Pharmaceutical applications of cyclodextrins . . ." J. Pharm. Sci. (1996) vol. 85, No. 10, pp. 1017-1025.*
Hirayama, F. et al "Cyclodextrin-based controlled drug release system" Adv. Drug. Delivery Rev. (1999) vol. 36, pp. 125-141.*
Robson, P. "Therapeutic aspects of cannabis and cannabinoids" Br. J. Psychiatry (2001) vol. 178, pp. 107-115.*
Hoogstraate, J. et al "Drug delivery via the buccal mucosa" PSTT (1998) vol. 1, No. 7, pp. 309-316.*
Yu, C. et al "Enhancement of solubility, dissolution rate, and oral bioavailability . . ." Drug Dev. Ind. Pharm. (1989) vol. 15, No. 4, pp. 609-620. (abstract only).*
Y. Shoyama et al., Journal of Natural Products, vol. 46, No. 5, 1983, p. 633 to 637.
Pekka Jarho et al., Life Sciences, vol. 63, No. 26, 1998, p. 381 to 384.
David W. Pate et al., Life Sciences, vol. 58, No. 21, 1996, p. 1846 to 1860.
Pekka Jarho et al., Life Sciences, vol. 58, No. 10, 1996, p. 181 to 185.
Hancock, *Exp. Opin. Invest. Drugs*, 9(8):1723-1729 (2000).
Szente et al, *Adv. Drug. Deliv. Rev.*, 36:17-28 (1999).
Hedges et al, *Chem. Rev.*, 98:2035-2044 (1998).
Garrett et al, *J. Pharm. Sci.* (Abstract), 63(7):1056-1064 (2006).
Challa et al, "Cyclodextrins in Drug Delivery: An Updated Review", Journal, AAPS-*PharmSciTech*, pp. 1-55, published Oct. 14, 2005.
Pitha et al, *J. Pharm. Sci.* (Abstract), 75(2):165-167 (2006).
Mannila et al, *Eur. J. Pharm. Sci.*, (Article), pp. 1-7, published 2005.
Mannila et al, *J. Pharm. Sci.*, 96(2):312-319 (2007).
Manilla, Cyclodextrins in Intraoral Delivery of $\Delta^9$-tetrahydrocannabinol and Cannabidiol, Doctoral Dissertation, University of Kuopio (May 11, 2007).
Hazekamp et al, *Eur. J. Pharm. Sci.*, 29:340-347 (2006).
Mannila et al, *Life Sciences*, 78:1911-1914 (2006).
Pitha et al, *J. Pharm. Sci.*, 76(10):788-790 (1987).

* cited by examiner

*Primary Examiner*—Leigh C Maier
(74) *Attorney, Agent, or Firm*—Sughrue Mion, PLLC

(57) ABSTRACT

The present invention is directed to the novel use of complexes of cyclodextrin. In particular the invention is directed to a complex of a cyclodextrin selected from the group consisting of α-CD, β-CD and γ-CD and a cannabinoid selected from the classical cannabinoid-group consisting of cannabinol, tetrahydrocannabinol and cannabidiol.

11 Claims, 2 Drawing Sheets

NATURAL CYCLODEXTRIN COMPLEXES

TECHNICAL FIELD OF THE INVENTION

The present invention describes the use of natural cyclodextrins (α-CD, β-CD and γ-CD) in sublingual and buccal formulations in order to improve the dissolution rate and bioavailability of selected cannabinoids, especially classical cannabinoids such as cannabidiol (CBD), cannabinol (CBN) and $\Delta^9$-tetrahydrocannabinol (THC).

BACKGROUND OF THE INVENTION

Cannabinoids are a group of compounds which are ligands to cannabinoid receptors ($CB_1$, $CB_2$) found in the human body (Pertwee, 1997). Cannabinoids were originally found from *Cannabis sativa* L., the origin of marijuana and hashish. Over the last few years, marijuana or its components have been reported in the scientific literature to counter the symptoms of a broad range of conditions including multiple sclerosis and other forms of muscular spasm, including uterine and bowel cramps; movement disorders; pain, including migraine headache; glaucoma, asthma, inflammation, insomnia, and high blood pressure. There may also be utility for cannabinoids as an oxytoxic, anxiolytic, anti-convulsive, anti-depressant and anti-psychotic agent (Williamson and Evans, 2000), or anti-cancer agent, as well as an appetite stimulant.

Nowadays over 60 chemically related compounds, collectively classified as cannabinoids, have been isolated from *Cannabis sativa* L., including tetrahydrocannabinol (THC), cannabidiol (CBD) and cannabinol (CBN). In addition, various synthetic ligands for cannabinoid receptors have been developed during the last few years. The cannabinoids usually divided in the groups of classical cannabinoids, non-classical cannabinoids, aminoalkylindol derivatives and eicosanoids (Pertwee, 1997). Classical cannabinoids are isolated from *Cannabis sativa* L. or they can comprise synthetic analogs of these compounds. Non-classical cannabinoids are bi- or tricyclic analogs of tetrahydrocannabinol (THC) (without the pyran ring); aminoalkylindols form a group which differs structurally substantially from classical and non-classical cannabinoids.

The pharmacological and toxicological studies of cannabinoids have been focused mainly on THC (commercially available under the name Dronabinol) which in 1985 was approved by the FDA for the treatment of chemotherapy associated nausea and vomiting, and later for AIDS-associated wasting and anorexia. Dronabinol is a synthetic analog of THC which is marketed in USA as Marinol. In Marinol, THC is dissolved in sesame oil and it is administered orally as a capsule containing 5 or 10 mg of THC. The major problem of THC in oral administration is its low bioavailability due to its poor dissolution properties and high first-pass metabolism. The bioavailability of orally ingested mc ranges from only 6% to approximately 20% depending on the drug vehicle employed.

Cyclodextrins (CDs) are cyclic oligosaccharides consisting of (α-1,4)-linked α-D-glucopyranose units, with a lipophilic central cavity and a hydrophilic outer surface (Frömming and Szejtli, 1994). CDs are able to form inclusion complexes with many drugs by taking up the whole drug, or more commonly, the lipophilic moiety of the molecule, into the cavity. The most abundant natural CDs are α-cyclodextrin (α-CD), β-cyclodextrin (β-CD) and γ-cyclodextrin (γ-CD), containing six, seven, and eight glucopyranose units, respectively. Of these three CDs, β-CD appears to be the most useful pharmaceutical complexing agent because of its cavity size, availability, low cost and other properties. There are also a number of CD derivatives available, such as hydroxypropyl-β-CD and methylated CDs. One of the major differences between natural CDs and the CD derivatives above is that natural CDs have been shown to form low solubility complexes with various drugs, as opposed to water-soluble CDs derivatives. Water-soluble CD derivatives form only water-soluble complexes with lipophilic drugs.

In drug formulations, CDs have been used mainly to increase the aqueous solubility, stability and bioavailability of various drugs, food additives and cosmetic ingredients (Frömming and Szejtli, 1994). In addition, CDs can also be used to convert liquid compounds into microcrystalline powders, prevent drug-drug or drug-additive interactions, reduce gastro-intenstinal or ocular irritation, and reduce or eliminate unpleasant taste and smell.

Studies dealing with the use of CDs with cannabinoids (classical, non-classical and aminoalkylindol derivatives) are referred to in the following publications. Shoyama et al. (1983) have reported that THC forms an inclusion complex with natural β-CD with increasing chemical stability of THC. Shoyama et al. (1983) prepared the solid THC/β-CD inclusion complex by mixing THO and β-CD in a methanol/water solution and hypothesised that CDs (in general) may also be used to improve the aqueous solubility, membrane permeability and bioavailability of THC. Jarho et al. (1998) have reported that HP-β-CD increases the aqueous solubility of THC and that co-administration of small amounts of a water-soluble polymer, hydroxypropyl methylcellulose (HPMC) enhances the complexation between HP-β-CD and THC. In addition, Song et al. (2000) and Porcella et al. (2001) have recently used HP-β-CD to solubilize the aminoalkylindol derivative WIN-55212 in topical ophthalmic formulations.

SUMMARY OF THE INVENTION

The present invention is directed to a novel use of a complex between a specific group of cyclodextrins and cannabinoids. Specifically, the invention relates to a complex of a cyclocextrin selected from the group consisting of α-CD, β-CD and γ-CD, and a cannabinoid selected from the classical cannabinoid-group consisting of cannabinol, tetrahydrocannabinol and cannabidiol.

Specifically, the present invention is directed to the use of the complex for the preparation of a pharmaceutical composition for sublingual or buccal administration. The invention is also directed to pharmaceutical compositions containing such a complex which are intended for sublingual or buccal administration, for example in the form of a tablet, capsule, chewing gum, lozenge or pill.

Furthermore, the invention is directed to a method for treating an individual, such as a human, for a condition responsive to treatment with a cannabinoid, the method comprising administering sublingually or buccally to said individual a sufficient amount of a complex of a cyclodextrin selected from the group consisting of α-CD, β-CD and γ-CD and a cannabinoid selected from the classical cannabinoid group consisting of cannabinol, tetrahydrocannabinol and cannabidiol.

In addition, the present invention is also directed to a process for the preparation of a complex of a cyclodextrin selected from the group consisting of α-CD, β-CD and γ-CD, and a cannabinoid selected from the classical cannabinoid-group consisting of cannabinol, tetrahydrocannabinol and cannabidiol, the process comprising combining the selected cyclodextrin with the selected cannabinoid in solution, in a heterogenous state or in the solid state, including using methods such as precipitation, freeze-drying, spray-drying, kneading, grinding, slurry-method, co-precipitation, and neutralization, and optionally separating said complex.

DETAILED DESCRIPTION OF THE INVENTION

Figure 1:
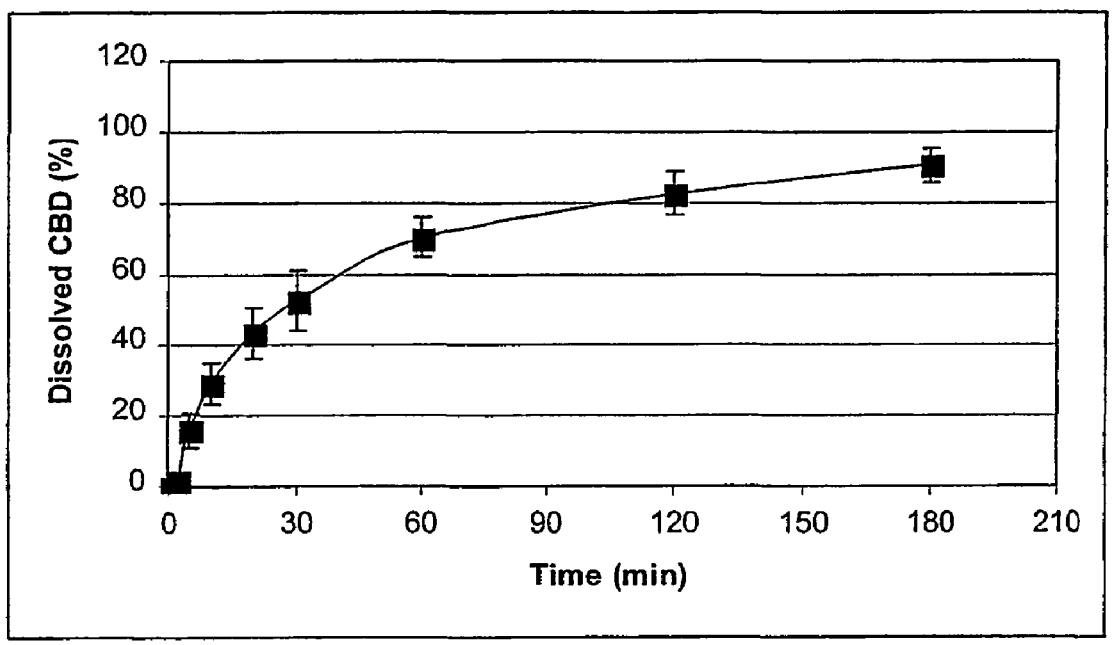
FIG. 1 shows the dissolution profile of CBD from a gelatine capsule.

The present invention describes the use of natural CDs to improve the dissolution rate, absorption rate and bioavailability of classical cannabinoids when administered sublingually or buccally.

Sublingual and buccal drug administration routes are potential alternatives for cannabinoid therapy due to the circumvention of the first-pass metabolism resulting in increased bioavailability of the cannabinoids. The absorption of the cannabinoids across the oral mucosa may also increase the onset of action compared to absorption of cannabinoids from the GI-tract (traditional oral formulations). One of the major requirements of sublingual/buccal drug administration is a fast dissolution of the drug at the site of absorption (sublingual area in the mouth). This is due to the fact that only the dissolved drug is able to absorb into the systemic circulation and that in sublingual drug administration the patient may swallow (due to increased salvation) the dosage form before the release of the drug. The present innovation is based on the finding that insoluble cannabinoid/natural cyclodextrin complexes can be used to significantly increase the dissolution rate of cannabinoids which can be used in sublingual cannabinoid formulations. The increased dissolution rate of the cannabinoids is due to the better solubility/dissolution properties of the solid cannabinoid/natural cyclodextrin inclusion complexes compared to pure cannabinoid, whereas the dissolution rate of pure cannabinoids is too slow for sublingual drug formulations.

The solid cannabinoid/natural CD complexes can be prepared by simply stirring cannabinoids and natural CDs in an aqueous solution which leads to the precipitation of solid complexes (i.e., the cannabinoid molecules are inside of the CD cavity and form inclusion complexes).

The complexation of cannabinoids with natural CDs produce low solubility complexes that leads to the precipitation of solid "true" cannabinoid/natural-CD complexes. The "true" cannabinoid/natural-CD complexes significantly improve the dissolution, solubility and bioavailability properties of cannabinoids, and thus improves the pharmaceutical usefulness of CDs in cannabinoid formulations.

As discussed above, the bioavailability of THC is 6-20% after oral administration. THC is commercially available as a capsule containing 5-10 mg of THC (Marinol).

In sublingual and buccal formulations a smaller dose of cannabinoids can be administered due to by-pass of the first-pass metabolism. Jarho et al. showed that with a 40% solution of HP-β-CD, a 1 mg/ml solution of THC can be obtained. Thus, it can be calculated that (after freeze-drying) 400 mg of HP-β-CD would be needed to complex 1 mg of THC. The same formulation can be prepared theoretically with 3.6 mg of natural β-CD (assuming 1:1 stochiometry for the complex) which increases the usefulness of CD technology in sublingual and buccal drug formulations.

The novel inclusion complexes of the invention can be prepared in conventional manner, known to a person skilled in art. Such complexes are typically made by dissolving a selected cannabinoid in a selected CD, and the product, which precipitates, is the cannabinoid/CD-complex. The amounts of cannabinoids and CD are selected to give desired complexation efficiency which also depends on the complexation constant between cannabinoid and CD. The complexation constant (K) between cannabinoids and CDs are usually in a range of 1 $M^{-1}$ to 100 000 $M^{-1}$. Typically cannabinoid and CD are used in a weight ratio (dry weight to dry weight) ranging between 1:3 and 1:1000.

The formation of inclusion complex can be facilitated by using solvents, such as organic solvents, for example methanol or ethanol. The temperature can vary to some degree, but it is typically for convenience the ambient temperature.

The cannabinoid/CD-solution can also be freeze-dried or spray-dried, to form a powder to be included in a pharmaceutical preparation.

The cannabinoid CD inclusion complexes can also be prepared under heterogenous conditions (suspension) and in solid phase. These methods include methods such as kneading, grinding, and the so-called slurry method. In solution, methods such as co-precipitation and neutralization can be used to prepare the solid inclusion complexes.

The pharmaceutical preparation can be any suitable pharmaceutical preparation for sublingual and buccal administration.

The pharmaceutical preparation according to the invention contains the said complex in pharmaceutically acceptable amounts together with pharmaceutically acceptable carriers, adjuvants or vehicles known in the art. The pharmaceutical composition may be in a dosage form suitable for sublingual or buccal use, such as tablets, capsules, lozenges, pills, pastilles, chewing gum etc. Suitable vehicles for making such administration forms are for example starch, lactose, sucrose, sorbitol, talc, stearates, and gums etc. All such formulations are made using per se known formulation techniques.

The therapeutic dose to be given to a patient in need of treatment will vary depending i.a. on the body weight and age of the patient, the particular condition being treated as well as the manner of administration and are easily determined by a person skilled in the art. Generally a concentration of 0.1 mg to 500 mg cannabinoid, typically 0.1 mg to 50 mg per unit dose, to be given for example 1 to 4 times a day, would be suitable for most purposes.

The following examples illustrate the invention without limiting the same in any way.

EXAMPLE 1

In this example the effect of natural β-CD on the dissolution characteristics of CBD have been described.

A powder containing a CBD/β-CD inclusion complex was prepared by the precipitation method. In this method a methanol solution of CBD was added dropwise to an aqueous β-CD solution and after equilibration the white precipitate (CBD/β-CD inclusion complex) was isolated and dried. The HPLC analysis of the powder showed that 9.1 mg of the powder contained 1.0 mg of CBD. All the following dissolution experiments were made in 2% RM-β-CD dissolution medias (pH 6.6) to ensure the free solubility of CBD.

FIG. 1 shows the dissolution profile (dissolved CBD as a function of time) of CBD from a gelatine capsule containing 1.0 mg of pure CBD and 99 mg of lactose (Mean±SD, n=6).

Figure 2:
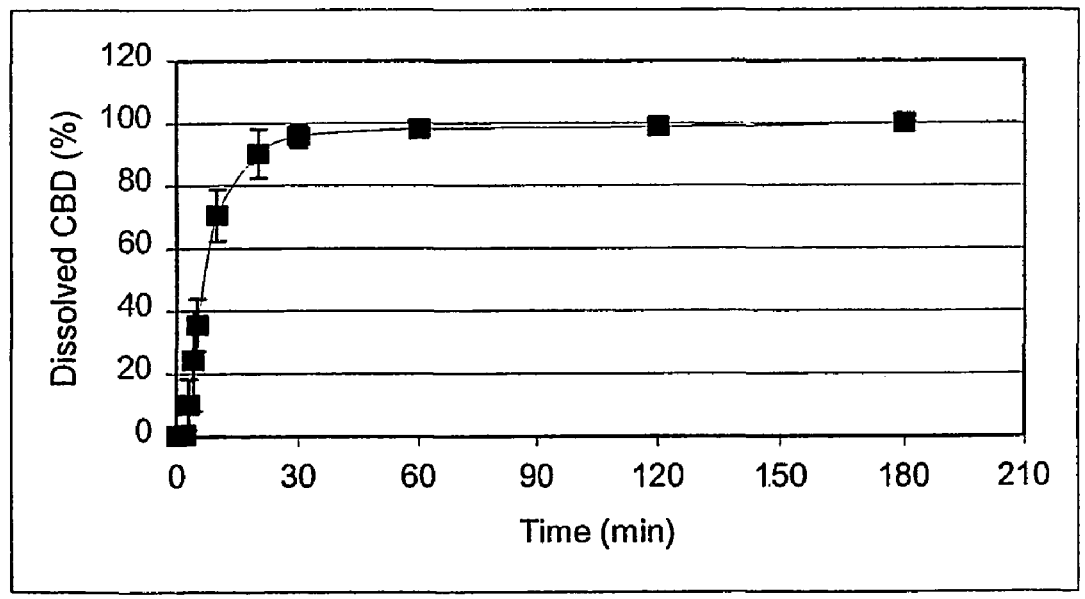
FIG. 2 shows the dissolution profile of a natural β-CD/CBD complex from a gelatine capsule.

FIG. 2 shows the same data with a capsule containing 9.1 mg of natural β-CD/CBD-complex (equivalent to 1 mg of THC) and 90.9 mg of lactose (Mean±SD, n=4).

FIGS. 1 and 2 show that the complexation of CBD with natural β-CD significantly increases the dissolution rate of CBD. With a β-CD/CBD formulation, CBD is fully dissolved in 30 minutes. Without β-CD, the dissolution rate is much slower and CBD is not fully dissolved in 3 hours.

EXAMPLE 2

In this example the effect of natural γ-CD on the dissolution characteristics of CBD have been described.

A powder containing a CBD/γ-CD inclusion complex was prepared by the precipitation method. In this method a methanol solution of CBD was added dropwise to an aqueous γ-CD solution and after equilibration the white precipitate (CBD/γ-CD inclusion complex) was isolated and dried. The HPLC analysis of the powders showed that 7.7 mg of the powder above contained 1.0 mg of CBD. All the following dissolution experiments were made in 2% RM-β-CD dissolution medias (pH 6.6) to ensure the free solubility of CBD.

Figure 3:
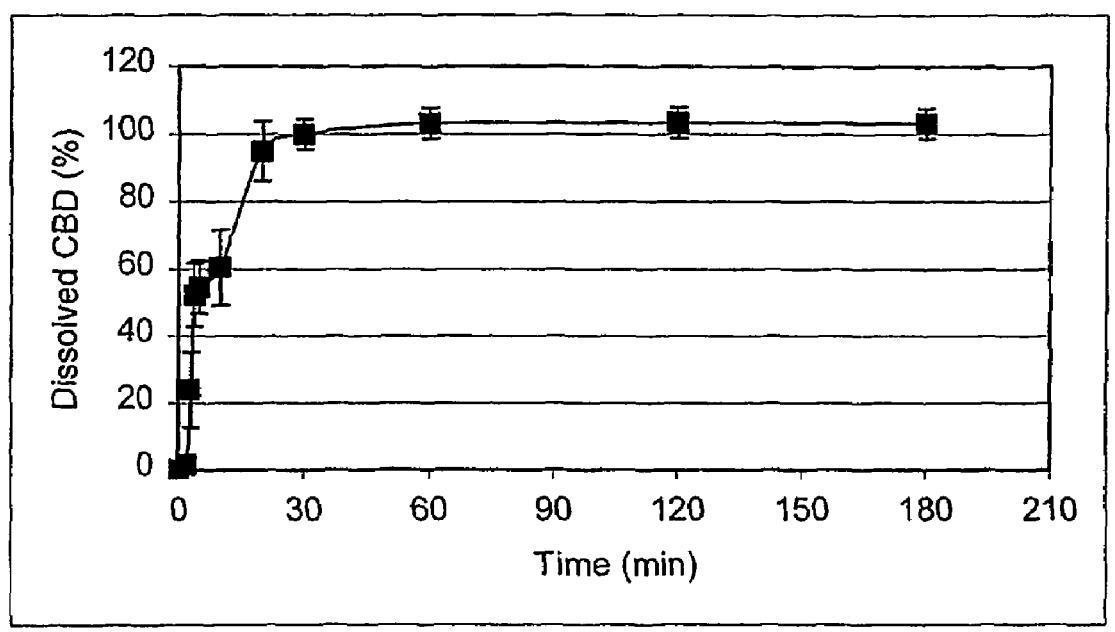
FIG. 3 shows the dissolution profile of a natural γ-CD/CBD complex from a gelatine capsule.

FIG. 1 shows the dissolution profile (dissolved CBD as a function of time) of CBD from a gelatine capsule containing 1.0 mg of pure CBD and 99 mg of lactose (Mean±SD, n=6). FIG. 3 shows the same data with a capsule containing 7.7 mg of a natural γ-CD/CBD-complex (equivalent to 1 mg of THC) and 92.3 mg of lactose (Mean±SD, n=4).

FIGS. 1 and 3 show that the complexation of CBD with natural γ-CD significantly increases the dissolution rate of CBD. With a γ-CD/CBD formulation, CBD is fully dissolved in 30 minutes. Without γ-CD, the dissolution rate is much slower and CBD is not fully dissolved in 3 hours.

REFERENCES

Frömming K-H, Szejtli J: Cyclodextrins in pharmacy. Kluwer Academic Publishers, Dortrecht, 1994.
Higuchi T, Connors K A: Phase-solubility techniques. Adv. Anal. Chem. Instr. 4: 117-212, 1965.
Porcella A, Maxia C, Gessa G L, Pani L: The synthetic cannabinoid WIN55212-2 decreases the intraocular pressure in human glaucoma resistant to conventional therapies. Eur. J. Neurosci. 13: 409-412, 2001.
Pertwee, R G: Pharmacology of cannabinoid CB1 and CB2 receptors. Pharmacol. Ther. 74: 129-180, 1997.
Shoyama Y, Morimoto S, Nishioka I: Cannabis XV: preparation and stability $\Delta^9$-tetrahydrocannabinol-β-cyclodextrin inclusion complex. J. Nat. Prod. 46: 633-637, 1983
Song Z-H, Slowey C-A: Involvement of cannabinoid receptors in the intraocular pressure lowering effects of WIN55212-2. J. Pharm. Exp. Ther. 292: 136-139, 2000.
Williamson E M, Evans F J: Cannabinoids in clinical practise. Drugs 60: 1303-1314, 2000.'
Zhang M-Q, Rees D C: A review of recent application of cyclodextrins for drug discovery. Exp. Opin. Ther. Patents. 9: 1697-1717, 1999.

The invention claimed is:

1. A complex comprising:
   (A) γ-cyclodextrin, and
   (B) a tetrahydrocannabinol,
   wherein said complex is an insoluble complex.

2. The complex of claim 1, wherein the tetrahydrocannabinol is $\Delta^9$-tetrahydrocannabinol.

3. The complex of claim 1 or 2, wherein the tetrahydrocannabinol and γ-cyclodextrin are present in the complex in a weight ratio, based on dry weight, of 1:3-1:1000.

4. A pharmaceutical composition comprising the complex of claim 1 or 2, and at least one pharmaceutically acceptable carrier, adjuvant or additive.

5. The pharmaceutical composition of claim 4, wherein the tetrahydrocannabinol and γ-cyclodextrin are present in the complex in a weight ratio, based on dry weight, of 1:3-1:1000.

6. The pharmaceutical composition of claim 4, wherein said composition is in a form suitable for sublingual or buccal administration.

7. The pharmaceutical composition of claim 6, wherein said composition is in the form of a tablet, a capsule, a chewing gum, a lozenge, a pill or a pastille.

8. A method of treatment of a subject comprising administering to a subject afflicted with or suffers from nausea, muscular spasms, multiple sclerosis, uterine cramps, bowel cramps, pain, migraine headache, glaucoma, asthma, inflammation, insomnia, high blood pressure, anxiety, convulsions, depression or psychosis, an effective amount of the complex of claim 1 or 2.

9. The method of claim 8, wherein administering is sublingually or buccally administering.

10. The method of claim 8, wherein said complex is administered such that from 0.1 to 500 mg of tetrahydrocannabinol are administered per unit dose per day.

11. The method of claim 10, wherein said complex is administered such that from 0.1 to 50 mg of tetrahydrocannabinol are administered per unit dose per day.

* * * * *